United States Patent
Cirile

(10) Patent No.: US 8,679,467 B1
(45) Date of Patent: Mar. 25, 2014

(54) DYELESS ALL-DAY FACIAL HAIR COLOR

(71) Applicant: Jim Cirile, Los Angeles, CA (US)

(72) Inventor: Jim Cirile, Los Angeles, CA (US)

(*) Notice: Subject to any disclaimer, the term of this patent is extended or adjusted under 35 U.S.C. 154(b) by 0 days.

(21) Appl. No.: 13/754,726

(22) Filed: Jan. 30, 2013

(51) Int. Cl.
*A61Q 5/06* (2006.01)
*A61Q 5/00* (2006.01)
*A61K 8/00* (2006.01)

(52) U.S. Cl.
USPC ............ 424/70.6; 424/70.1; 424/70.11

(58) Field of Classification Search
None
See application file for complete search history.

(56) References Cited

U.S. PATENT DOCUMENTS

| | | | |
|---|---|---|---|
| 7,763,241 B2 * | 7/2010 | Steigerwald et al. | 424/70.6 |
| 2003/0031637 A1 * | 2/2003 | Loginova et al. | 424/63 |
| 2005/0008604 A1 * | 1/2005 | Schultz et al. | 424/70.14 |
| 2009/0151086 A1 * | 6/2009 | Brun | 8/405 |

FOREIGN PATENT DOCUMENTS

WO   WO 2008066243 A1 *   6/2008

OTHER PUBLICATIONS

Creagel Crystal, "Creagel® Crystal", Cosmetics Innovations and Technologies Sarl, 2007, p. 1-2.*
CosmeticsINFO.org, "Isohexadecane", <http://cosmeticsinfo.org/ingredient_details.php?ingredient_id=2261>, Oct. 2012, p. 1-2.*
CosmeticsINFO.org, "Isononyl Isononanoate", <http://www.cosmeticsinfo.org/ingredient_details.php?ingredient_id=2175>, May 2012, p. 1-2.*
CosmeticsINFO.org, "Tocopheryl Acetate", <http://www.cosmeticsinfo.org/ingredient_details.php?ingredient_id=585>, Apr. 2010, p. 1-2.*
In-cosmetics, "Euxyl® PE 9010", <http://www.in-cosmetics.com/en/Exhibitors/107619/Schuelke-Mayr-GmbH/Products/565966/euxyl-PE-9010>, © 2012, p. 1-4.*

* cited by examiner

*Primary Examiner* — Tracy Vivlemore
*Assistant Examiner* — Monica Shin
(74) *Attorney, Agent, or Firm* — Omni Legal Group; Omid E. Khalifeh

(57) ABSTRACT

A dyeless all-day coloring formula that can be applied easily using a brush or other similar application tool to facial hair is an ideal way to mask the gray hair color often brought about by aging follicles. Such a formulation may have similar properties to mascara more commonly used by women to enhance the appearance of their eyelashes. However, the dyeless facial hair coloring formula will overcome the disadvantages commonly associated with currently available facial hair coloring solutions.

9 Claims, No Drawings

DYELESS ALL-DAY FACIAL HAIR COLOR

CROSS-REFERENCE TO RELATED APPLICATIONS

None

BACKGROUND

The following is a tabulation of some prior art that presently appears relevant:

| U.S. Patents | | | |
|---|---|---|---|
| Pat. No. | Kind Code | Issue Date | Patentee |
| 5,800,825 | A | Sep. 1, 1998 | McMullen |
| 8,236,063 | B2 | Aug. 7, 2012 | Reichert et al. |

U.S. Patent Application Publications
    None Found
Foreign Patent Document
    None found
Nonpatent Literature Documents
    None found

NOTICE OF COPYRIGHT AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

DISCUSSION OF THE RELATED ART

An assortment of cosmetics have been proposed to help overcome the problem of aging follicles and graying hair. They take different forms and perform different functions. From creating the illusion of length to minimizing the appearance of grays, some cosmetics may darken, thicken, lengthen, and/or define features. However, all heretofore known products take either the form of a liquid, cake, cream, or dye.

Although modern coloring cosmetics have various formulas, most contain the same basic components of pigments, oils, waxes, and preservatives. These are commonly marketed to women as a method of enhancing beauty, and the stigma associated with such products have caused most men to avoid their use. Companies seeking to capitalize on this masculine aversion have rebranded common cosmetics to make their use appear more acceptable.

Some men have turned to beard dyes produced by companies such as Just for Men® Mustache & Beard. The product is designed to mask gray facial hair by dyeing the individual strands of unpigmented hair. While these products do work, their use comes with an assortment of undesirable consequences.

Those who use regular dyes have been known to experience a variety of unpleasant reactions to the chemicals contained therein. These include redness, itching, scaling, rash, and even open sores. Such products are full of harsh chemicals like ammonia, coal, or tar derivatives which irritate the skin and give off foul odors.

Because facial hair grows rapidly, men using these dyes need to constantly reapply as gray roots come in. Furthermore, the manufacturers of the products have been unsuccessful in their attempts to make application easy. The application processes are long and messy. They are inelegant and require a cumbersome application process involving using mixing chemicals while wearing rubber gloves and then directly inhaling harsh, concentrated chemical fumes for the duration of the 5-10 minute application process, followed by a shower or thorough face-washing.

Thus, some men have grown weary of this process and have chosen instead to live with the gray facial hair caused by aging follicles, or to simply shave off their mustaches and beards.

Other solutions have been proposed to contend with difficult problem of graying facial hair. One such product, WolfsHead® "beardye," replaces some of the harmful chemicals found in Just for Men® with henna. This henna-based dye eliminates some of the negative consequences caused by Just for Men® Mustache & Beard, but introduces more of its own.

Henna-based dyes are also difficult and messy to apply. They require several applications before the full effect is noticeable on the user, and the resulting color is less pronounced than with a dye. Therefore, this is not an ideal solution to the man who desires all the benefits of using a beard dye without the drawbacks, hassle and potential harmful side effects.

In brief, even though coloring cosmetics have been proposed in the past, all of the those heretofore known suffer from a number of disadvantages:
  (a) the known coloring cosmetics require a lengthy dye and then rinse application process;
  (b) the known coloring cosmetics contain harsh chemicals such as ammonia, coal, and tar additives;
  (c) the known coloring cosmetics are odiferous;
  (d) the known coloring cosmetics cannot be washed off easily;
  (e) the known coloring cosmetics may cause redness, itching, scaling, and can penetrate open sores causing an unsightly rash or even infection; and
  (f) the known coloring cosmetics have become undesirable to many men seeking to avoid the harmful consequences associated with beard dyes.

Various methods for pigmenting male facial hair have been proposed. However, none of the foregoing combine the characteristics of the present invention. Therefore, there is a need for a dyeless facial hair color that can be applied daily without agitation. The present invention effectuates these needs.

SUMMARY

A dyeless all-day temporary coloring formula that can be applied easily using a brush or other similar application tool to facial hair is an ideal way to mask the gray hair color often brought about by aging follicles. Such a formulation may have similar properties to mascara more commonly used by women to enhance the appearance of their eyelashes. However, all the mascara products heretofore known have their own set of disadvantages when used as facial hair color, specifically, a quick fade time and lack of durability (product can rub or wash off easily.)

A new formulation is envisioned that will allow users to avoid detriments while enjoying the benefits of an easy to use mascara-like solution. Such a formulation may be comprised of the ingredients commonly found in mascara with the quantities adjusted, useless additives removed, and new ingredients incorporated to produce a unique product that wears longer and is more resistant to smudging and rub-off than all other known long-wearing mascaras.

By way of example and not limitation, carnauba wax may be used instead of beeswax, which is often found in standard long-wearing mascara. Carnauba is a plant-based wax like candelilla and jojoba and is the hardest natural wax known. As with other natural waxes, it blends well with oils, fats, and other waxes thereby raising their melting points and hardness. Carnauba also has a melting point of 87 degrees Celsius which is 13 degrees higher than that of beeswax. Using carnauba instead of beeswax increases the melting point of the mascara and its resistance to fading and smudging while worn.

Applicant's hair color will be less susceptible to smearing and will dry more quickly than standard mascara. Furthermore, the ingredients comprising Applicant's formula contain none of the harsh chemicals found in many currently available facial hair dyes. The effects will be immediately noticeable following a single application which can be done using an included in-cap brush, similar but not limited to common eyelash mascaras.

In one embodiment, Applicant's formulation may allow the user to wear it longer while being more resistant to smudging because it contains nearly twice the amount of the isododecane/ethylene/propylene copolymer than the known long-wearing mascaras. Long-wearing mascara typically contains 14.0% of this substance. Volatile substances such as the aforementioned copolymer are used in mascara to yield a more waterproof mascara. However, greater concentrations of the isododecane/ethylene/propylene copolymer in not commonly used in mascara as it makes it more difficult to remove and can lead to damage or removal of eyelashes. Those concerns however are not relevant for the purpose of coloring facial hair.

Applicant has found, in conjunction with a different formulation of other ingredients commonly found in mascara, that Applicant can substantially reduce the unwanted characteristics of those previously known formulations. Therefore, Applicant's formulation comprises more than double the amount of isododecane/ethylene/propylene copolymer found in those formulations.

Modifying the concentrations of compounds commonly found in long-lasting mascaras effectuate the desirous properties of Applicant's invention. These compounds further include isododocane, trimethylsiloxysilicate/isododecane, parafin, isononyl isononanoate, phenoxyethanol/ethylhexylgycerin, and tocopherylacetate. Moreover, certain commonly found compounds are removed from the known long-lasting mascaras in order to effectuate Applicant's needs. These include vp/eicosene copolymer, hydrogenated poluisobutene, caprylic/capric triglyceride and paraffin. Finally, it is desirable to replace harmful pigments found in mascara with naturally occurring ingredients such as black iron oxide.

ADVANTAGES

Thus several advantages of one or more aspects are to provide a dyeless all-day facial hair color that:
(a) that can be applied quickly and without dripping;
(b) that wears longer than heretofore known mascaras;
(c) that is more resistant to smudging than the known mascaras;
(d) does not contain the harsh chemicals and additives of known dyes;
(e) that does not emit a foul odor;
(f) that can be removed using hot water and soap;
(g) that does not cause redness, itching, scaling;
(h) will not penetrate open sores causing and unsightly rash or even infection; and
(i) is a desirable way for men seeking to avoid the disadvantages of other facial hair coloring techniques to maintain a youthful appearance.

These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus the scope of the embodiments should be determined by the claims that are appended and their legal equivalents, rather than by the examples given.

The description of the invention which follows, together with the accompanying examples should not be construed as limiting the invention to the examples shown and described, because those skilled in the art to which this invention pertains will be able to devise other forms thereof within the ambit of the appended claims.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details. In other instances, well-known structures and functions have not been shown or described in detail to avoid unnecessarily obscuring the description of the embodiments.

The preferred embodiment related to a facial hair color formula that is developed to stay on the user's hair longer while being more resistant to smudging and wash-off than known long-wearing mascaras. Applicant's formula can be used as a substitute to current methods men commonly use to color unwanted gray in facial hair. The past techniques included dyes with skin irritants as well as more natural alternatives that are messy to apply and take several applications to deliver results. Applicant's formulation overcomes these and other problems associated with the known coloring formulations.

In the preferred embodiment, Applicant's formulation can be applied directly to the beard. In one embodiment, a brush may be used to facilitate this process. Drying occurs quickly, virtually eliminating the risk of accidental dripping of the formula. Drying has been observed in as little as 15 seconds, making Applicant's formulation nearly twice as fast as currently known mascaras. Masking of the gray hair can be observed instantly after the formula is applied, and there is no need to wash off anything until user decides to remove the formula from their face. The preferred formulation is specifically designed to last longer than known mascaras while being more resistant to rub-off, wash-off and smudging.

As with all mascaras, pigments known in the art can be employed in whatever range is desired to yield a mascara having the desired color and intensity of color. Iron oxide can be used alone or in conjunction with other pigments known in the art and may be included in an amount most preferably 12% by weight of the formula. In addition, one or more of the following ingredients may be included or be substituted with an appropriate equivalent. They are given by way of example, not by limitation: iron oxide; black iron oxide; and red iron oxide.

EXAMPLES OF THE PREFERRED EMBODIMENTS

In order to more fully teach what the Applicant regards as his invention, the following examples are given. It should be understood that the formulations set forth in the Examples are given by way of example only and are not to be construed as limiting the scope of the invention, except so far as they yield a dyeless all-day facial hair color having the desired properties and characteristics.

Dry formula mascaras have been proposed in the past. By way of example, the following chart illustrates a common formulation of the same with the percentages being given by weight of the mascara:

| INCI NAME | CAS NO. | % |
|---|---|---|
| ISODODOCANE | 13475-82-6 | 30.0 |
| TRIMETHYLSILOXYSILICATE/ ISODODECANE | 56275-01-5/ 93685-81-5 | 17.0 |
| ISODODECANE/ ETHYLENE/PROPYLENE COPOLYMER | 13475-82-6/ 9010-79-1 | 14.0 |
| VP/EICOSENE COPOLYMER | 28211-18-9 | 10.0 |
| BEES WAX | 8012-89-3 | 5.2 |
| ISONONYL ISONONANOATE | 59219-17-5 | 5.0 |
| HYDROGENATED POLYISOBUTENE | 68937-10-0 | 3.0 |
| CAPRYLIC/CAPRIC TRIGLYCERIDE | 65381-09-1 | 3.0 |
| PARAFFIN | 8002-74-2 | 2.0 |
| PHENOXYETHANOL/ ETHYLHEXYLGLYCERIN | 122-99-6/ 70445-33-9 | 0.6 |
| TOCOPHERYL ACETATE | 7695-91-2 | 0.2 |
| PIGMENT | | 10.0 |

The following ingredients are an example of Applicant's dyeless all-day facial hair color with the percentages being given by weight:

| ICI NAME | CAS NO. | % |
|---|---|---|
| ISODODECANE/ ETHYLENE/PROPYLENE COPOLYMER | 13475-82-6/ 9010-79-1 | 34.5 |
| ISODODOCANE | 13475-82-6 | 22.2 |
| TRIMETHYLSILOXYSILICATE/ ISODODECANE | 56275-01-5/ 93685-81-5 | 15.0 |
| PARAFFIN | 8002-74-2 | 5.2 |
| CARNAUBA WAX | 8015-86-9 | 3.8 |
| ISONONYL ISONONANOATE | 59219-17-5 | 3.5 |
| ISOHEXADECANE | 93685-80-4 | 3.0 |
| PHENOXYETHANOL/ ETHYLHEXYLGLYCERIN | 122-99-6/ 70445-33-9 | 0.6 |
| TOCOPHERYLACETATE | 7695-91-2 | 0.2 |
| BLACK IRON OXIDE | CI. 77499 | 12.0 |
| TOTAL | | 100.0% |

In one embodiment of the above disclosed Applicant's formulation, the isododecane/ethylene/propylene copolymer may exist in the following ratio:
  isododecane/ethylene: 88%
  propylene copolymer: 12%

In one embodiment of the above disclosed Applicant's formulation, trimethylsiloxysilicate/isododecane may exist in the following ratio:
  trimethylsiloxysilicate: 80%
  isododecane: 20%

In one embodiment of the above disclosed Applicant's formulation, phenoxyethanol/ethylhexyl glycerin may exist in the following ratio:
  phenoxyethanol: 90%
  ethylhexyl glycerin: 10%

Moreover, in various embodiments, black iron oxide may be substituted with different pigments. These substitutions will allow different colored formulations for different hair colors. By way of example and not limitation, black iron oxide may be replaced with a black iron oxide and iron oxide formulation. This formulation would result in a dark brown colored dyeless hair color.

The above mentioned formational is in contrast with an all-black dyeless hair color which would result if only black iron oxide was used as the pigment.

Further, a formulation comprising red iron oxide, black iron oxide, and iron oxide would result in a brown colored dyeless hair color. In one embodiment of the dyeless all-day facial hair color, the percentage amount by weight of the various pigment formulations would remain the same. In other words, the pigments may combine to form 12% of the entire formulation.

The facial hair color formula may also include pigments known in the art but not listed here. The foregoing composition is able to become sufficiently dry such that it would not easily smear and will remain relatively dry to the touch in about 30 seconds after application. After drying, the formula remains sufficiently water soluble such that it could be removed with hot water and soap, or other forms of makeup removers should the user so desire.

CONCLUSIONS, RAMIFICATIONS, AND SCOPE

While a particular form of the invention has been illustrated and described, it will be apparent that various modifications can be made without departing from the spirit and scope of the invention. For example, the black color in one embodiment of the solution will be effectuated using black iron oxide even though the inventor contemplates the possibility of using other colors and varying methods of effectuating the same. Accordingly, is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Particular terminology used when describing certain features or aspects of the invention should not be taken to imply that the terminology is being refined herein to be restricted to any specific characteristics, features, or aspects of the dyeless hair color with which that terminology is associated. In general, the terms used in the following claims should not be constructed to limit the dyeless hair color to the specific embodiments disclosed in the specification, unless the above description section explicitly define such terms. Accordingly, the actual scope encompasses not only the disclosed embodiments, but also all equivalent ways of practicing or implementing the disclosed foam apparatus. The above description of embodiments of the dyeless hair color is not intended to be exhaustive or limited to the precise form disclosed above or to a particular field of usage. While specific embodiments of, and examples for, the dyeless hair color are described above for illustrative purposes, various equivalent modifications are possible which those skilled in the relevant art will recognize.

While certain aspects of the dyeless hair color are presented below in particular claim forms, the inventor contemplates the various aspects of the dyeless hair color in any number of claim forms. Accordingly, the inventor reserves the right to add additional claims after filing the application to pursue such additional claim forms for other aspects of the dyeless hair color.

What is claimed is:

1. A dyeless all-day facial hair color comprising:
a mixture comprising isododecane, and ethylene-propylene copolymer;
isododecane;
a mixture comprising trimethylsiloxysilicate and isododecane;
paraffin;
carnauba wax;
isononyl isononanoate;
isohexadecane;
a mixture comprising phenoxyethanol and ethylhexylglycerin;
tocopheryl acetate; and
pigment.

2. The facial hair color of claim 1 comprising:
a mixture comprising isododecane and ethylene-propylene copolymer;
22.2 wt. % isododecane;
15 wt. % a mixture comprising trimethylsiloxysilicate and isododecane;
5.2 wt. % paraffin;
3.8 wt. % carnauba wax;
3.5 wt. % isononyl isononanoate;
3.0 wt. % isohexadecane;
0.6 wt. % a mixture comprising phenoxyethanol and ethylhexylglycerin;
0.2 wt. % tocopheryl acetate; and
12 wt. % pigment.

3. The facial hair color of claim 1 where the pigment is black iron oxide.

4. The facial hair color of claim 1 where the pigment is comprised of black iron oxide and iron oxide.

5. The facial hair color of claim 1 where the pigment is comprised of black iron oxide, red iron oxide, and iron oxide.

6. An all-day facial hair color comprising:
a mixture comprising isododecane, and ethylene-propylene copolymer
up to 34.5 wt. % of the composition;
isododecane up to about 22.2 wt. % of the composition;
a mixture comprising trimethylsiloxysilicate and isododecane up to about 15 wt. % of the composition;
paraffin up to about 5.2 wt. % of the composition;
carnauba wax up to about 3.8 wt. % of the composition;
isononyl isononanoate up to about 3.5 wt. % of the composition;
isohexadecane up to about 3.0 wt. % of the composition;
a mixture comprising phenoxyethanol and ethylhexylglycerin up to about 0.6 wt. % of the composition;
tocopheryl acetate up to about 0.2 wt. % of the composition; and
pigment up to about 12 wt. % of the composition.

7. The facial hair color of claim 6 where the pigment is black iron oxide.

8. The facial hair color of claim 6 where the pigment is comprised of black iron oxide and iron oxide.

9. The facial hair color of claim 6 where the pigment is comprised of black iron oxide, red iron oxide, and iron oxide.

\* \* \* \* \*